US009402965B2

(12) United States Patent
Holtwick et al.

(10) Patent No.: US 9,402,965 B2
(45) Date of Patent: Aug. 2, 2016

(54) EJECT BUTTON FOR A MEDICAMENT DELIVERY DEVICE

(75) Inventors: Marc Holtwick, Frankfurt am Main (DE); Ilona Eggert, Frankfurt am Main (DE); Christopher Nigel Langley, Warwickshire (GB); Aled Meredydd James, West Midlands (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 93 days.

(21) Appl. No.: 14/119,857

(22) PCT Filed: May 24, 2012

(86) PCT No.: PCT/EP2012/059758
§ 371 (c)(1),
(2), (4) Date: Nov. 22, 2013

(87) PCT Pub. No.: WO2012/160165
PCT Pub. Date: Nov. 29, 2012

(65) Prior Publication Data
US 2014/0081215 A1  Mar. 20, 2014

(30) Foreign Application Priority Data
May 25, 2011 (EP) .................................. 11167539

(51) Int. Cl.
*A61M 5/34* (2006.01)
(52) U.S. Cl.
CPC ................. *A61M 5/34* (2013.01); *A61M 5/343* (2013.01); *A61M 5/348* (2013.01); *A61M 5/344* (2013.01)
(58) Field of Classification Search
CPC ....... A61M 5/34; A61M 5/343; A61M 5/344; A61M 5/348

USPC ................................................... 604/240, 533
See application file for complete search history.

(56) References Cited

U.S. PATENT DOCUMENTS

| 4,822,343 | A | | 4/1989 | Beiser | |
|---|---|---|---|---|---|
| 5,271,527 | A | | 12/1993 | Haber et al. | |
| 5,314,412 | A | * | 5/1994 | Rex ......................... | A61M 5/19 222/137 |
| 5,569,210 | A | * | 10/1996 | Moen .................... | A61B 5/1427 600/573 |
| 2006/0217740 | A1 | * | 9/2006 | Ghannoum ......... | A61F 9/00736 606/107 |

(Continued)

FOREIGN PATENT DOCUMENTS

| EP | 0747087 A2 | 12/1996 |
|---|---|---|
| EP | 1342449 A2 | 9/2003 |

(Continued)

*Primary Examiner* — Quynh-Nhu H Vu
(74) *Attorney, Agent, or Firm* — McDonnell Boehnen Hulbert & Berghoff LLP (57) ABSTRACT

A medicament delivery device comprises a housing having a longitudinal axis, a medicament delivery mechanism within the housing, a dispense interface disengagement actuator and a detachable dispense interface. The interface is moveable between a first operative position in which the dispense interface is securely engaged and at least partially contained within the housing, and a second non-operative position in which the dispense interface is partially engaged and at least partially extending from the housing such that it can be detached from the housing manually. The travel of the dispense interface from the first position to the second position is along the longitudinal axis in a direction away from the housing and the movement from the first to the second position is actuated by the dispense interface disengagement actuator.

10 Claims, 5 Drawing Sheets

(56) References Cited

U.S. PATENT DOCUMENTS

2010/0217206 A1    8/2010   Lum et al.
2011/0106016 A1    5/2011   Wei
2011/0276008 A1*   11/2011   Matthias ................ 604/201

FOREIGN PATENT DOCUMENTS

| EP | 1704840 A1 | 9/2006 |
|---|---|---|
| JP | 2011-509754 A | 3/2011 |

* cited by examiner

EJECT BUTTON FOR A MEDICAMENT DELIVERY DEVICE

CROSS REFERENCE TO RELATED APPLICATIONS

The present application is a U.S. National Phase Application pursuant to 35 U.S.C. §371 of International Application No. PCT/EP2012/059758 filed May 24, 2012, which claims priority to European Patent Application No. 11167539.3 filed May 25, 2011. The entire disclosure contents of these applications are herewith incorporated by reference into the present application.

FIELD OF INVENTION

The present invention relates to an improved dispense interface, forming part of a handheld medicament delivery device.

BACKGROUND

Certain medical conditions require patients to self-administer medicament(s) over a long period of time, perhaps years. Where possible such medicaments will be formulated for oral delivery which helps with patient compliance. Due to the nature of the medicament (e.g. insulin) oral delivery is not always possible and other administration routes are necessary. Self administration by injection for chronic conditions such as diabetes is therefore relatively common.

Common to most injection devices is the need to use a replaceable dispense interface prior to injection of a medicament. Typically, a disposable needle located within a needle hub is replaced and discarded with every injection. Unfortunately, users of such medical devices may lack manual dexterity, have visual impairment and/or suffer weakness in the hands such that replacing the dispense interface is often difficult.

Furthermore, some injection devices allow the injection of multiple medicaments, either sequentially or simultaneously. Such devices often require a further dispense interface or hub to bring the cartridges containing the medicament(s) into fluid communication with a common outlet. Unlike a conventional needle hub, a dispense interface for a multiple medicament device does not allow a simple screwthread connection between the device and the dispense interface. As the dispense interface must align and fluidly engage with two medicament cartridges the dispense interface must generally be connected in an axial manner.

The drug delivery device may have a single dispense interface. This interface may be configured for fluid communication with the reservoir in the case of a single medicament device or, in the case of a combination therapy device, a primary reservoir and with a secondary reservoir of medicament containing at least one drug agent. The drug dispense interface can be a type of outlet that allows the two or more medicaments to exit the system and be delivered to the patient.

An example of such a device is shown in granted U.S. Pat. No. 5,271,527 in the name of Habley. The Habley device shows a pharmaceutical dispenser for dispensing two or more medicaments from respective medicament cartridges. Attached to said device is a manifold that may be removed by pressing and holding manifold release buttons located on either side of the manifold to overcome the frictional fit and remove the manifold. Such a co-ordinated manoeuvre is difficult to people of reduced manual dexterity and increases the risk of safety issues, such as needle stick injuries. Furthermore, such a removal mechanism provides uncertainty for both the device and the user during the attachment and disconnection procedure as to whether and when the manifold and the medicament in the device are in fluid communication. A partially connected or disconnected cartridge may be in fluid engagement with the device leading to potential loss of medicament or in some cases incorrect dosing.

An object of the present invention is therefore to provide a reliable, safe mechanism for removing a dispense interface from a medicament delivery device.

SUMMARY

According to the present invention there is provided a medicament delivery device comprising
    a housing having a longitudinal axis,
    a medicament delivery mechanism within the housing,
    a detachable dispense interface moveable between
    (i) a first operative position in which the dispense interface is securely engaged and at least partially contained within the housing, and
    (ii) a second non-operative position in which the dispense interface is partially engaged and at least partially extending from the housing such that it can be detached from the housing manually,
    the travel of the dispense interface from the first position to the second position being along the longitudinal axis in a direction away from the housing, and
    an actuator for disengagement of the dispense interface,
    the movement from the first to the second position being actuated by the actuator.

In certain embodiments, the dispense interface actuator comprises at least one biasing element which biases the dispense interface away from the housing. Alternatively or additionally, the dispense interface actuator may comprise one or more pushrods which only act on the dispense interface when actuated.

In certain embodiments the housing and dispense interface are each provided with at least one inter-engageable element that holds the dispense interface in the first position (for example against the bias of the biasing element). For example, the inter-engageable elements may constitute a latch.

The or each biasing element is conveniently a spring (e.g. a leaf or coil spring).

In certain embodiments, the dispense interface disengagement actuator comprises a user activated button. The button may act directly or indirectly mechanically to separate the inter-engageable elements on the housing and the dispense interface. Alternatively, the button may be part of an electromechanical assembly that causes separation of the inter-engageable elements.

In certain embodiments, the housing and dispense interface are a frictional fit. It will be understood that in those embodiments where the actuator comprises a biasing element, the frictional fit must be balanced with the force of the biasing element to allow movement of the dispense interface from the first position to the second position without total disengagement of the dispense interface from the housing.

In the second non-operative position, the dispense interface can be detached from the housing manually. This may be understood that the dispense interface can be detached from the housing without using a tool, or without further support from the device. For example, no further button press or menu item selection is needed to remove the dispense interface.

In certain embodiments, the inter-engageable elements are constituted by one or more retaining arms on the dispense interface and one or more grooves, rebates, slots, channels or recesses in the housing.

The term "medicament delivery device" as used herein, means a device capable of administering a dose of one or more medicaments to a patient. Such devices may administer fixed and/or variable doses of medicament to a patient. Hand-held medicament delivery devices are sometimes called 'pen-type' devices. The medicament delivery mechanism employed by such devices is preferably electromechanical, utilising a motor and gearing to drive a piston rod, although manual delivery mechanisms incorporated into electrically controlled or configured devices may also be envisaged.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compounds, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HC1 or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopaedia of Pharmaceutical Technology.

Pharmaceutically acceptable solvates are for example hydrates.

BRIEF DESCRIPTION OF THE DRAWINGS

Embodiments of then invention will now be described by way of example only with reference to the accompanying drawings in which.

DETAILED DESCRIPTION

References to the device in the following detailed description are intended to refer to the device as referenced in the appended figures and not to when the device is in a use state. Furthermore, the figures are intended to be schematic representations to highlight relevant functionality of the present invention and therefore unnecessary structures have been omitted from the device for clarity. The relative dimensions of the device are also illustratory only. Reference to 'distal' and 'proximal' are intended to refer to the end of the device where medicament delivery occurs and the opposite end pointing away from the delivery site respectfully.

Figure 1:
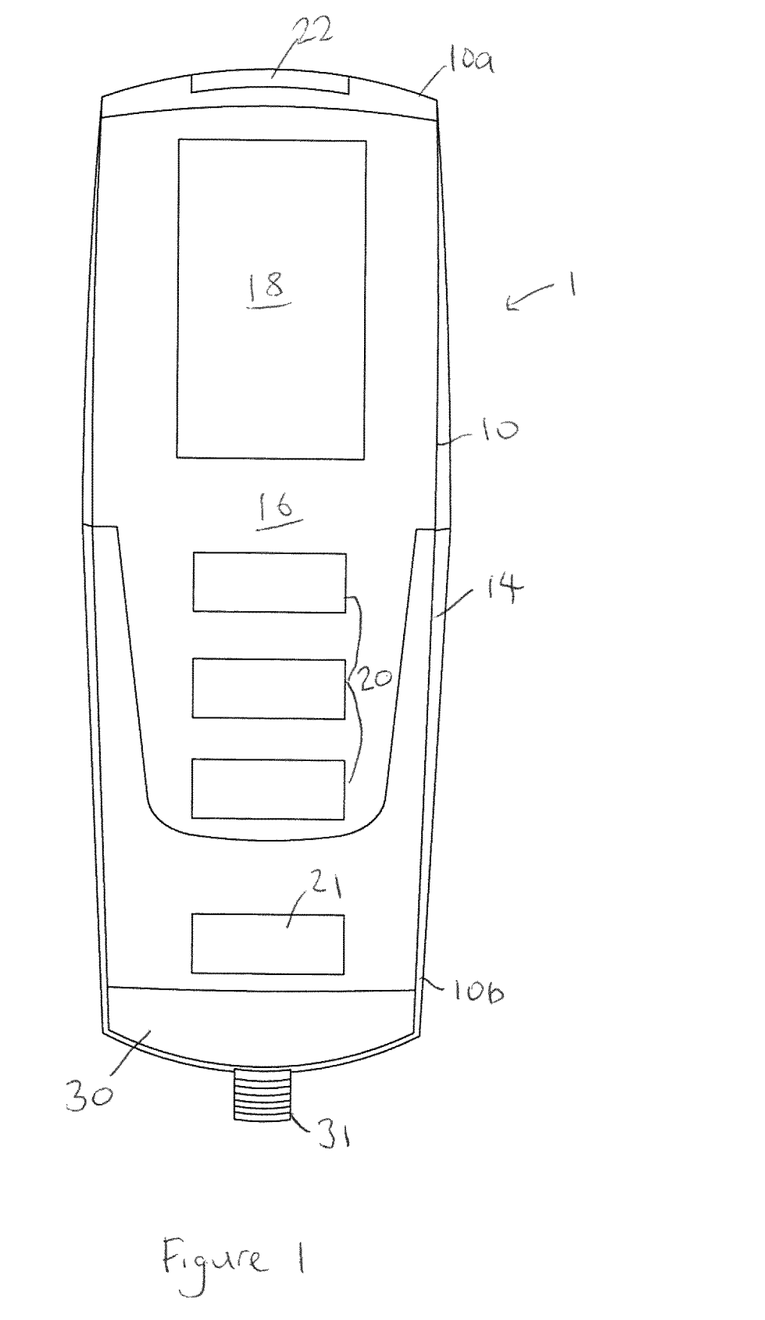
FIG. 1 is a plan view of a medicament delivery device according to the present invention.

The medicament delivery device 1 illustrated in FIG. 1 comprises a housing 10 having a proximal end 10a and a distal end 10b. At the distal end 10b, the housing is shaped to receive a removable end cap or cover (not shown). This end cap and the housing 10 (at its proximal end) are shaped to provide a form fit connection so that once the cap is slid onto the distal end 10b of the housing 10, the frictional fit between the cap and the housing 10 prevents the cap from inadvertently falling off the housing 10. It will be understood that in other embodiments (not shown) other means of releasably securing the cap to the housing such as snap-fit may be employed.

The interior surface of the cap and the outer surface of the housing 10 at its proximal end 10b are shaped such that there is only one possible configuration in which the cap properly fits onto the distal end 10b of the housing 10. Such an arrangement is preferable because it provides certainty in the alignment of components of the cap with components of the housing 10, as will be explained below.

The housing 10 contains a micro-processor control unit, PCB, an electromechanical drive train, a battery, and at least one medicament reservoir. A cartridge holder 14 can be removably attached to the housing 10 and may contain one or more cartridges of medicament. The cartridge holder 14 is configured so as allow the replacement of the medicament cartridges as necessary. The medicament delivery device 1 can be used to administer a computed dose of a medicament (or medicaments) through a needle assembly, such as a double ended needle assembly. It will be understood that the cap and housing arrangement described is equally applicable to needleless jet injectors.

A control panel region is provided on one major face 16 of the housing 10 and comprises a digital OLED display 18 towards the distal end 10a of the housing 10 along with a plurality of human interface elements (buttons 20 in the embodiment shown) that can be manipulated by a user to set and inject a medicament dose. It will be understood that in other embodiments (not shown) different display technology such as LCD displays can be used. The buttons 20 also allow navigation through menu structures displayed on the OLED display 18. An eject button 21 described in greater detail below is provided at the distal end 10b of the device 1. A dose button 22 is provided in an end face of the housing 10 at its proximal end 10a.

In use, when the device is turned on, the digital display 18 shown in FIG. 1 illuminates and provides the user certain device information, preferably information relating to the medicaments contained within the cartridge holder 14. For example, the user is provided with certain information relating to both the contents of the cartridge and previous dose history.

At the distal end 10b of the housing is provided a dispense interface 30. The dispense interface 30 is configured to receive a needle assembly or hub (not shown) via a screw-thread connector 31. This needle hub can be configured to allow a dose dispenser, such as a conventional pen type injection needle assembly, to be removably mounted to the housing 10. It will be understood that the attachment between the dispense interface 30 and a needle hub is preferably a screw fit to allow standard 'type A' needles to be fitted to the dispense interface 30, although other attachment mechanisms as known in the art, such as Luer lock attachments may be used in other embodiments (not shown).

Figure 2:
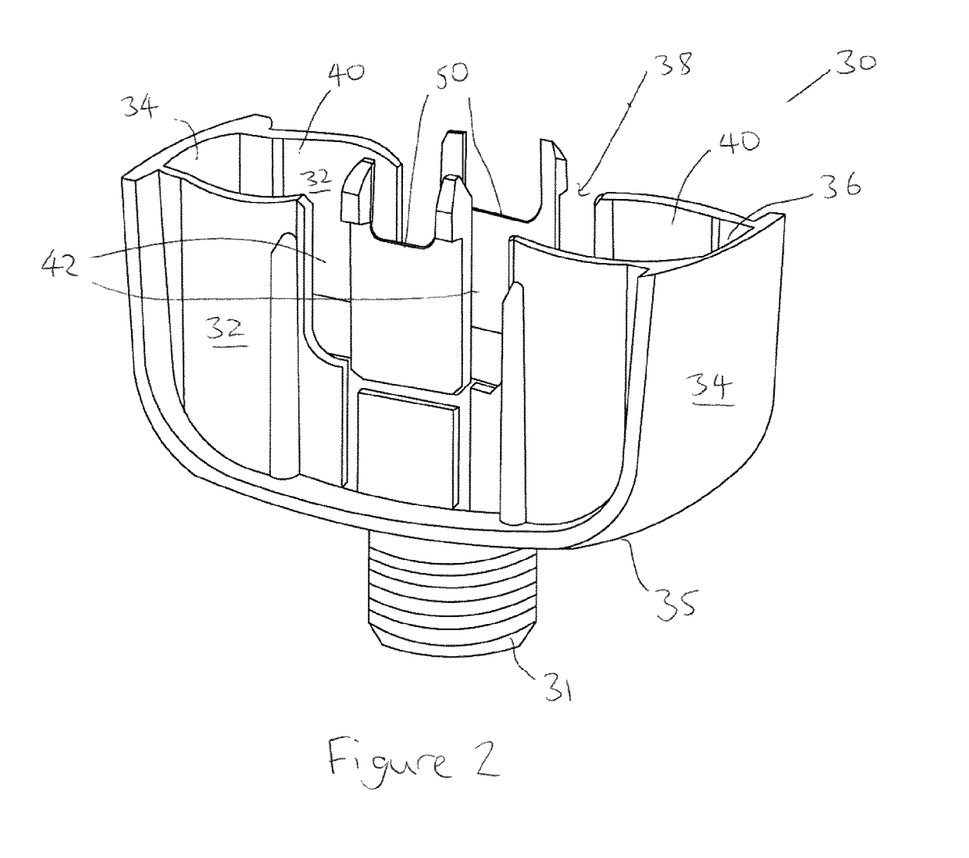
FIG. 2 is a perspective view of the dispense interface shown in FIG. 1.

The dispense interface 30 is shown in greater detail in FIG. 2. The dispense interface 30 has spaced apart front and rear sidewalls 32 joined by spaced apart end sidewalls 34 to define a housing. The distal end 35 of the dispense interface 30 is closed save for an orifice or septum through the threaded connector 31. The proximal end 36 of the dispense interface 30 is open and the sidewalls 32, 34 define a cavity 38. The front and rear sidewalls 32 are curved to define a pair of medicament cartridge receiving slots 40 within the cavity 38. Each of the front and rear sidewalls 32 has a cut away mid-section 42. Received within the housing is an inner assembly 50 described in more detail with reference to FIG. 3.

Although the present embodiment shows two cartridge receiving slots 40, embodiments may include a single receiving slot or multiple receiving slots. Furthermore, in the present embodiment, the dispense interface 30 is symmetrical and therefore can receive the bezel of a cartridge in either receiving slot 40. However, embodiments may provide size discrimination between cartridges to be made by, for example, only allowing a bezel of a particular size to be received within a specific cartridge receiving slot 40.

Figure 3:
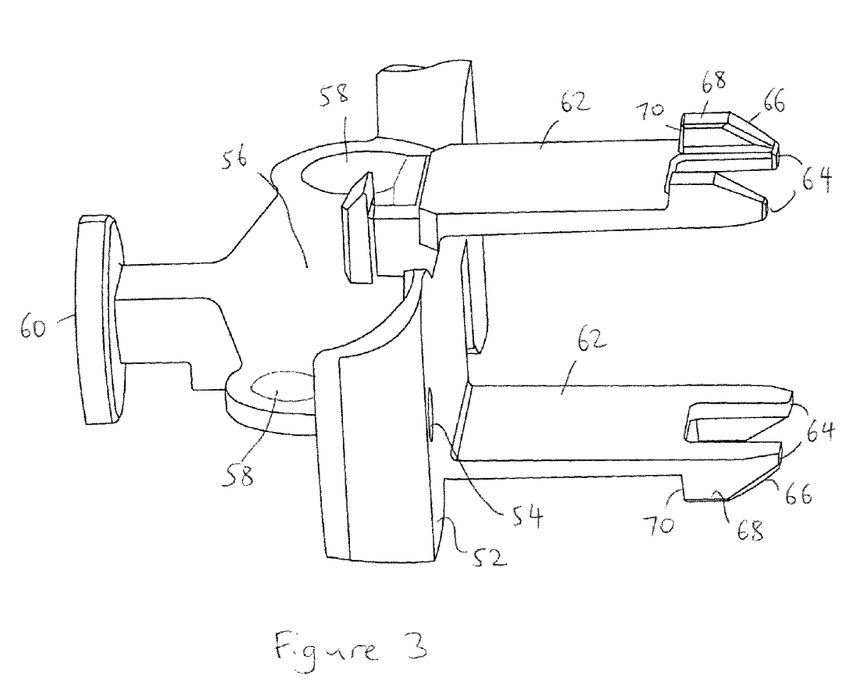
FIG. 3 shows the inner assembly of the dispense interface shown in FIG. 2.

FIG. 3 shows the inner assembly 50 of the dispense interface 30. A platform 52 defines a base of the dispense interface housing and a seating surface for medicament cartridges in use. At each side 54 of the platform 52 a needle (not shown) extends upwardly into the dispense interface housing 32, 34, which needles pierce the septa of the medicament cartridges when the dispense interface 30 is mounted on the device housing 10. Below the platform 52 and mounted within the dispense interface housing 32, 34 beneath its base is a valve assembly 56 comprising a pair of diaphragm valves 58. Mounted below the valves 58 is a septum 60 which is housed within the threaded connector 31. It will be understood that when mounted on the device housing 10, a valved flowpath exists from the medicament cartridge through the double ended needles, through the valve assembly and thereafter into an attached needle hub through the septum in the needle connector.

Extending upwardly from the platform 52 are a pair of spaced apart retaining arms 62 in the form of flexible tabs. A pair of spaced apart barbs 64 are integrally formed at the free ends of the tabs 62. When mounted in the dispense interface housing 32, 34 the tabs 62 are located within the cut outs 42 in the front and rear sidewalls 32 with the barbs 64 pointing away from the cavity 38 and extending above the sidewalls 32, 34. The barbs 64 have an outwardly tapering front surface 66, a flat mid surface 68 and a rear surface 70 perpendicular to the tab 62 itself. The barbed tongues 62, 64 constitute part of the attachment and release mechanism of the dispense interface 30 as will be described below.

Figure 4A:
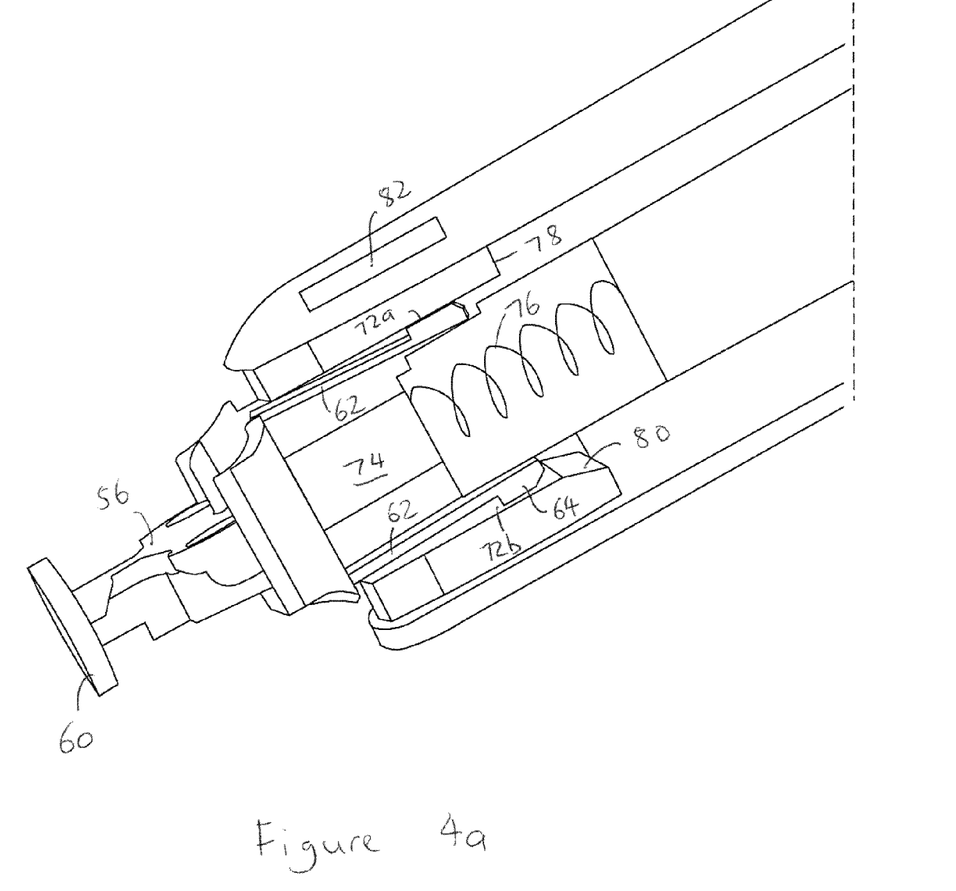
FIG. 4a shows a partial skeleton view of the dispense interface and the device shown in FIG. 1 when the dispense interface is in an unlocked orientation with respect to the device.
Figure 4B:
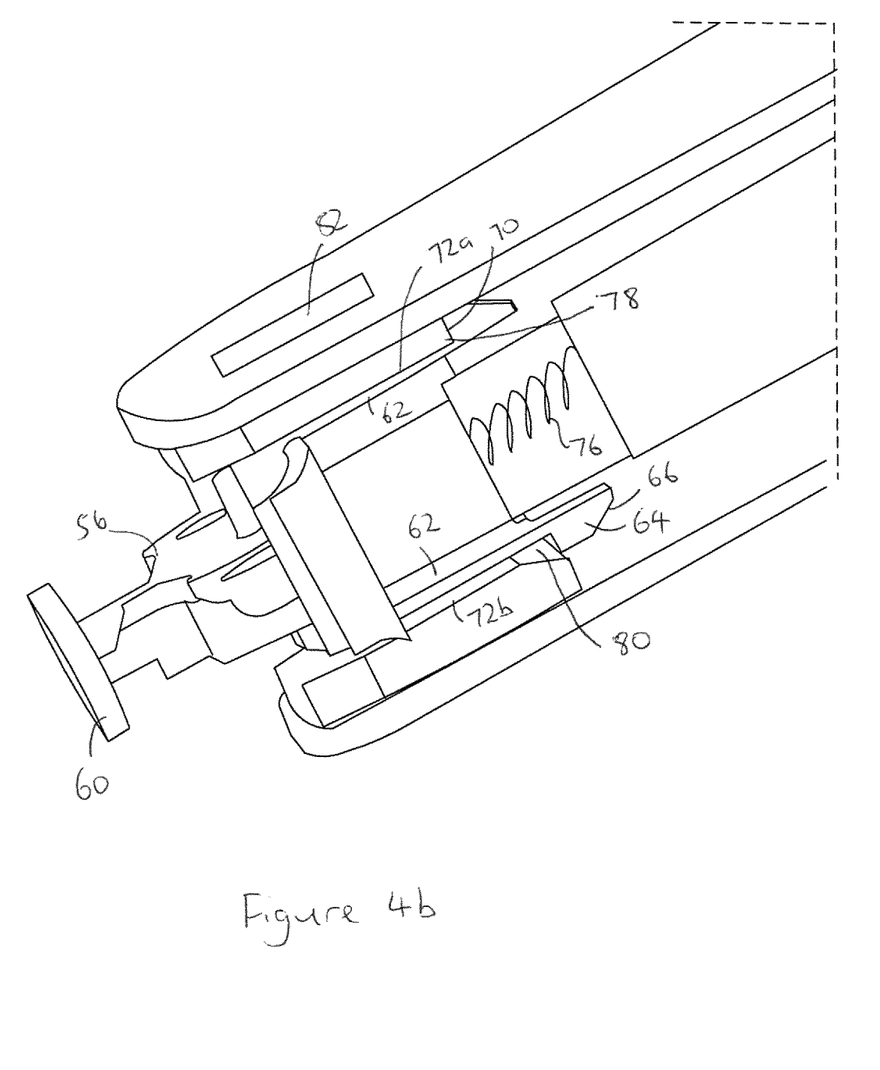
FIG. 4b shows a partial skeleton view as per FIG. 4a, with the dispense interface in a latched or locked position with respect to the device.

FIG. 4a shows a partial skeleton view of the dispense interface 30 both prior to connection with the distal end 10b of the device 1 and after disconnection with the device 1 in its partially engaged position. As the dispense interface 30 is placed onto the device, the barbs 64 slide over inwardly facing main surfaces of a pair of mounting plates 72a, 72b. As the user continues to press the dispense interface 30 into the device, the interface 30 via hammer 74 compresses spring 76 until the fully operative engaged position of FIG. 4b is reached. As shown in FIG. 4b, one of the mounting plates 72a has a rear blocking surface 78 which is perpendicular to its main surface, whereas the other mounting plate 72b has a chamfered rear surface 80. In the fully engaged position, the barbs 64 pass beyond the mounting surface 72 and flex outwardly (due to the inherent flexibility of the tabs). Although biased away from the housing 10 by the spring 76 the dispense interface 30 is locked into its operative position by virtue of engagement of one pair of barbs 64 on one of the tabs 62 with the rear blocking surface 78 of the mounting plate 72. The remaining pair of barbs 64 on the other tabs 62 are adjacent the chamfered rear surface 80 of the other mounting plate 72b but are not locked therewith. The importance of this will become clear in the following paragraph. It will be understood that in the case of a symmetrical dispense interface 30, the dispense interface can successfully be engaged with the housing of the device 1 in two orientations.

To unlock the dispense interface 30 from the distal end 10b of the device 1, the user presses the eject button 21 on the lower portion of the front face 16 of the device 1. The eject button 21, via a peg (not shown) extending from the rear of the eject button 21 through opening 82 presses onto the tab 62 whose barbs 64 are engaged with the blocking surface 78 of the mounting plate 72. By depressing the tab 62, the rear surface disengages the blocking surface 78 and since the other barbs 64 are unconstrained by the chamfered surface 80 of the other mounting plate 72b, the action of the compressed spring 76 now acts against the dispense interface 30 via the hammer 74 to force the dispense interface 30 away from the housing 10. In this position the dispense interface 30 is partially engaged with respect to the housing 10. The dispense interface 30 is prevented from fully disengaging with the device 10 due to the frictional engagement of the flat surfaces 68 of the barbs 64 with the mounting surface 72. It will be understood to the skilled person that the biasing of the spring 76 and the frictional forces can be balanced by changing one or more of the strength of the spring 76, the frictional coefficient of the barbs 64 and mounting plate 72 main surfaces, the area of contact between the barbs 64 and the mounting plate main surfaces or the flexibility of the tabs 62. This frictional force holding the dispense interface 30 in the partially engaged position with respect to the housing 1 is then low enough to allow a user to easily and manually remove the dispense interface 30 from the device. Furthermore, the dispense interface 30 release mechanism disengages the needles mounted within the dispense interface 30 from the cartridges mounted within the device 1, breaking the fluid communication between the dispense interface 30 and the medicament contained within the device 1 when in the partially engaged position shown in FIG. 4b. By ensuring that the dispense interface 30 is not in fluid communication with the medicaments stored within the device 1 the risk of loss of medicament is eliminated. Furthermore, the device is able to perform procedures that rely on the lack of fluid engagement such as detection of the position of the bung of the cartridges within the device without risk of loss of medicament or potential under or over dosing.

Embodiments of the present invention may include the use of the packaging of the dispense interface 30 in the engagement and disengagement process. For example, with a dispense interface 30 not attached to the distal end 10b of the device 1, a user may present the distal end of the device to the packaging containing the dispense interface 30. It is envisaged that the dispense interface 30 is held within custom packaging, for example a plastic holder (not shown) and is open at the top of the housing such that the cavities 38 of the dispense interface 30 are accessible by the device 1. A tear strip may be used to prevent contamination of the dispense interface 30 prior to use.

In such embodiments, as the distal end 10b of the device 1 is presented to the dispense interface 30, the dispense interface 30 is received within the distal end 10b of the device 1 such as shown in FIG. 4a. By continuing to bring the device 1 and the dispense interface 30 together, the dispense interface 30 engages with the device via the engagement of one pair of barbs 64 on one of the tabs 62 with the rear blocking surface 78 of the mounting plate 72 as described above to the position shown in FIG. 4b above. Similarly, the dispense interface 30 may be removed from the device as described above, or in further alternative embodiments, the packaging of the dispense interface may unlock/disengage the dispense interface 30 from the device 1 automatically, for example by actuating the eject button of the device. Alternatively, other unlock release mechanisms can be used such as a spring loaded push fit.

The invention claimed is:

1. A medicament delivery device comprising:
   a housing having a longitudinal axis;
   a medicament delivery mechanism within the housing;
   a detachable dispense interface for delivering a medicament, wherein the dispense interface comprises a connector located at an end of the dispense interface and configured to receive a needle assembly, and wherein the dispense interface is moveable between
   (i) a first operative position in which the dispense interface is securely engaged and at least partially contained within the housing, and
   (ii) a second non-operative position in which the dispense interface is partially disengaged with and at least partially extending from the housing such that it can be detached from the housing manually, the travel of the dispense interface from the first position to the second position being along the longitudinal axis in a direction away from the housing; and
   an actuator for disengagement of the dispense interface,
   wherein the actuator is configured to actuate the travel of the dispense interface from the first to the second position along the longitudinal axis in the direction away from the housing.

2. The device of claim 1, wherein the actuator comprises at least one biasing element which biases the dispense interface away from the housing.

3. The device of claim 2, wherein the at least one biasing element is a spring.

4. The device of claim 1, wherein the actuator comprises one or more pushrods which only act on the dispense interface when actuated.

5. The device of claim 1, wherein the housing and dispense interface are each provided with at least one inter-engageable element that holds the dispense interface in the first position.

6. The device of claim 5, wherein the inter-engageable elements comprise a latch.

7. The device of claim 5, wherein the actuator comprises a user activated button.

8. The device of claim 7, wherein the button acts mechanically to separate the inter-engageable elements on the housing and the dispense interface.

9. The device of claim 5, wherein the inter-engageable elements comprise one or more retaining arms on the dispense interface and one or more grooves, rebates, slots, channels or recesses in the housing.

10. The device of claim 1, wherein the housing and dispense interface are a frictional fit, the frictional fit being balanced with the force imparted by the dispense interface disengagement actuator to allow movement of the dispense interface from the first position to the second position without total disengagement of the dispense interface from the housing.

* * * * *